United States Patent
Homan et al.

(10) Patent No.: US 8,208,708 B2
(45) Date of Patent: Jun. 26, 2012

(54) TARGETING METHOD, TARGETING DEVICE, COMPUTER READABLE MEDIUM AND PROGRAM ELEMENT

(75) Inventors: Robert Johannes Frederik Homan, Batenburg (NL); Drazenko Babic, Best (NL); Pieter Maria Mielekamp, Veldhoven (NL); Jan Timmer, Best (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 928 days.

(21) Appl. No.: 12/294,626

(22) PCT Filed: Mar. 15, 2007

(86) PCT No.: PCT/IB2007/050890
§ 371 (c)(1),
(2), (4) Date: Sep. 26, 2008

(87) PCT Pub. No.: WO2007/113703
PCT Pub. Date: Oct. 11, 2007

(65) Prior Publication Data
US 2010/0172541 A1    Jul. 8, 2010

(30) Foreign Application Priority Data
Mar. 30, 2006    (EP) .................................. 06112046

(51) Int. Cl.
*G06K 9/00*    (2006.01)
(52) U.S. Cl. .............................. 382/131; 382/132; 378/4
(58) Field of Classification Search .................. 382/131, 382/132; 378/62
See application file for complete search history.

(56) References Cited

U.S. PATENT DOCUMENTS

| | | | |
|---|---|---|---|
| 4,485,815 A | | 12/1984 | Amplatz et al. |
| 5,117,829 A | * | 6/1992 | Miller et al. .................. 600/427 |
| 5,212,720 A | | 5/1993 | Landi et al. |
| 5,371,778 A | * | 12/1994 | Yanof et al. ....................... 378/4 |
| 5,810,841 A | | 9/1998 | McNeirney et al. |
| 6,064,904 A | * | 5/2000 | Yanof et al. .................. 600/414 |

(Continued)

FOREIGN PATENT DOCUMENTS
EP    0930046 A2    7/1999
(Continued)

OTHER PUBLICATIONS

Noumeir R: "Fitting of ellipses from support function measurements" Acoustics, Speech, and Signal Processing, 2000. ICASSP '00. Proceeding S. 2000 IEEE International Conference on Jun. 5-9, 2000, vol. 6, pp. 2294-2297, XP010504761, ISBN: 978-0-7803-6293-2.

*Primary Examiner* — Alexander H Taningco (57) ABSTRACT

According to an exemplary embodiment a targeting method for targeting a first object from an entry point to a target point in an object (110) under examination is provided, wherein the method comprises selecting a two-dimensional image (301) of the object under examination depicting the entry point (305) and the target point (303) and determining a planned path (304) from the entry point to the target point, wherein the planned path has a first direction. Furthermore, the method comprises recording data representing a fluoroscopic image of the object under examination, wherein the fluoroscopic image is recorded under a second direction so that a normal of the image coincide with the first direction and determining whether the first object is on the determined planned path based on shape and/or position of the projection of the first object in the fluoroscopic image.

21 Claims, 5 Drawing Sheets

U.S. PATENT DOCUMENTS

| | | |
|---|---|---|
| 6,363,134 B1 | 3/2002 | Suzuki |
| 6,671,538 B1 * | 12/2003 | Ehnholm et al. .............. 600/425 |
| 7,327,872 B2 * | 2/2008 | Vaillant et al. ................ 382/154 |
| 7,810,996 B1 * | 10/2010 | Giphart et al. ................ 378/207 |
| 7,881,423 B2 * | 2/2011 | Tsuyuki et al. .................... 378/4 |
| 2003/0097060 A1 | 5/2003 | Yanof et al. |
| 2006/0036264 A1 | 2/2006 | Selover et al. |
| 2006/0115054 A1 * | 6/2006 | Yatsenko et al. .............. 378/207 |
| 2007/0036266 A1 * | 2/2007 | Kramp et al. .................... 378/62 |

FOREIGN PATENT DOCUMENTS

| | | |
|---|---|---|
| EP | 1103229 A | 5/2001 |

* cited by examiner

TARGETING METHOD, TARGETING DEVICE, COMPUTER READABLE MEDIUM AND PROGRAM ELEMENT

FIELD OF INVENTION

The invention relates to a targeting method, a targeting device, a system, a computer readable medium and a program element, in particular to a method for targeting a first object from an entry point to a target point in an object under examination.

TECHNICAL BACKGROUND

Percuteneous targeting of various types of cervico-thoracal, abdominal and limb lesions is most frequently based on image guided interventional approach. There are several clinical procedures where this approach is applied: biopsies, chemical and thermal ablations, pain management procedures etc, for example. Two of the most frequently used imaging techniques for the image guidance are ultrasonic (US) based and computer tomography (CT) based. The US guided procedures are characterized by an interactive needle advancement monitoring and relatively good visualization of compact anatomical structures, e.g. bones. However, this technique suffers from multiple drawbacks, poor visualization of anatomical structures filled with air, poor visibility when bony anatomy is superimposed on the structure of interest, low signal quality in obese patients (subcutaneous fat), for example. The CT guided interventions provide high contrast resolution distortion-less images and good visualization of the anatomical structures. The disadvantage of the technique is poor patient access and room sterility issues. An intervention room equipped with a rotational X-ray device is much more suitable for such procedures, but for most of the procedures the contrast resolution of the X-ray device is not sufficient.

SUMMARY OF THE INVENTION

It may be desirable to provide an efficient targeting method, a targeting device, a system, a computer readable medium and a program element usable in a targeting device.

This need may be met by a targeting method, a targeting device, a system, a computer readable medium and a program element according to the independent claims.

According to an exemplary embodiment a targeting method for targeting a first object from an entry point to a target point in an object under examination is provided, wherein the method comprises, selecting a two-dimensional image of the object under examination depicting the entry point and the target point and determining a planned path from the entry point to the target point, wherein the planned path has a first direction. Furthermore, the method comprises, recording data representing a fluoroscopic image of the object under examination, wherein the fluoroscopic image is recorded under a second direction so that a normal of the image coincide with the first direction, and determining whether the first object is on the determined planned path based on a shape of the projection of the first object in the fluoroscopic image.

According to an exemplary embodiment a targeting device for targeting a first object from an entry point to a target point is provided, the targeting device comprises a selecting unit adapted to select a two-dimensional image of the object under examination depicting the entry point and the target point and a determining unit adapted to determine a planned path from the entry point to the target point, wherein the planned path has a first direction. Furthermore, the targeting device comprises a recording unit adapted to record data representing a fluoroscopic image of the object under examination, wherein the fluoroscopic image is recorded under a second direction so that a normal of the image coincide with the first direction, wherein the determining unit is further adapted to determine whether the first object is on the determined planned path based on a shape of the projection of the first object in the fluoroscopic image.

According to an exemplary embodiment a system for targeting a first object from an entry point to a target point is provided, the system comprises a radiation source, a radiation detector, and a targeting device according to an exemplary embodiment of the present invention, wherein the radiation detector is adapted to record the data representing the fluoroscopic image.

According to an exemplary embodiment a computer readable medium is provided in which a program for targeting a first object from an entry point to a target point is stored, which program, when executed by a processor, is adapted to control a method comprising, electing a two-dimensional image of the object under examination depicting the entry point and the target point, determining a planned path from the entry point to the target point, wherein the planned path has a first direction, recording data representing a fluoroscopic image of the object under examination, wherein the fluoroscopic image is recorded under a second direction so that a normal of the image coincide with the first direction, and determining whether the first object is on the determined planned path based on a shape of the projection of the first object in the fluoroscopic image.

According to an exemplary embodiment a program element for targeting a first object from an entry point to a target point, which program, when executed by a processor, is adapted to control a method comprising, electing a two-dimensional image of the object under examination depicting the entry point and the target point, determining a planned path from the entry point to the target point, wherein the planned path has a first direction, recording data representing a fluoroscopic image of the object under examination, wherein the fluoroscopic image is recorded under a second direction so that a normal of the image coincide with the first direction, and determining whether the first object is on the determined planned path based on a shape/position of the projection of the first object in the fluoroscopic image.

It may be seen as the gist of an exemplary embodiment of the present invention that a targeting method for targeting a first object from an entry point to a target point is provided, wherein the method comprises the selecting of a two-dimensional image, e.g. a slice or slab, in which an entry point and a target point are visible. Based on this image a path, e.g. the direct line, between the entry point and the target point can be determined. This path represents a first direction from which a second direction can be derived in which second direction a consecutive fluoroscopic image can be taken or recorded. The fluoroscopic image is also a two-dimensional image which normal is parallel with the first direction, i.e. the fluoroscopic image is recorded in the direction of the determined path. By using this fluoroscopic image an efficient way to control the movement of the first object may be provided by observing the form or shape of the first object on this fluoroscopic image. This shape and/or position can be compared to a predetermined shape, e.g. with a 3D graphic projected onto the fluoroscopic image. When the actual shape and/or position deviate from the predetermined shape and/or position the first object deviate from the planned path. Thus, a comparison may be implemented by an image recognition program, for example.

The method may facilitate an efficient method for targeting and/or tracking of a first object which is inserted or injected into a second object under examination by observing the shape of the projected first object in a fluoroscopic image.

In this application the term "an image" relates to the actual image as well as to the recorded data from which, by using well known methods, the actual image can be reconstructed. This targeting method may be usable in the field of C-arm apparatuses and/or tomography apparatuses, e.g. a computed tomography apparatus. Preferably, the fluoroscopic images, i.e. the data representing the fluoroscopic images, are taken by using a C-arm apparatus.

In the following, further exemplary embodiments of the targeting method will be described. However, these embodiments apply also for the targeting device, the system, the computer readable medium and the program element.

According to another exemplary embodiment of the targeting method the two-dimensional image is selected as a slice of a three-dimensional image of the object under examination. Preferably, the three-dimensional image is reconstructed out of data recorded by a computer tomography apparatus. Depending on the application three-dimensional (3D) data can be acquired with a CT modality (apparatus), e.g. depending on contrast resolution or if diagnostic data is already present, MR modality (apparatus) or with a C-arm with which CT-like image quality can be reached depending on the number of images acquired during a rotational scan.

Using a three-dimensional image, e.g. a voxel representation, of a three-dimensional object as an initial image from which a two-dimensional image is selected, is an efficient way to ensure that at least one slice or slab of the three-dimensional image contains the entry point and the target point. The voxel representation can be efficiently reconstructed out of data recorded in a computer tomography (CT) with well known methods of reconstruction.

The determination of the two-dimensional image can, for example, be done by indicating within a 3D volume of the object under examination a start (entry) point and an end point. The 3D volume can be from a different modality or can be acquired ob the same modality with a rotational scan. For effective path planning it may furthermore be advantageous, in order to prevent vessel perforation, to perform the planning on a fused volume presentation where the CT-(like) oblique volume slab is combined with a 3D angiographic volume rendering of the same object. The relation between the volume data and the fluoroscopic images can, for example, be determined with a machine based registration method whereby a C-arm geometry is calibrated. If the 3D volume data is originating from a different modality the relation may, for example, be determined with a registration method.

In one exemplary aspect of the invention from the planned path a 3D graphical model is generated, which is visible inside the volume data. With the determined geometrical relation between the (detector) fluoroscopic images and the volume data the C-arm can be moved to the optimal entry point view and progression point view on base of the 3D graphical model, taking into account the bending of the C-arm and the perspective nature of the fluoroscopic images, wherein the calculations are done from volume coordinates to C-arm sensor coordinates. For each position of the C-arm the 3D graphical model of the planned path can be projected as a 2D graphic onto the fluoroscopic image. The position/shape of the object visible on the fluoroscopic image must be the same as the projected graphic, during insertion into the body to keep on the planned path. Furthermore the volume data inside the slice/slab containing the planned path can also be projected onto the fluoroscopic image. This way the surrounding structures around the planned path and the target are made visible. The contrast resolution of the fluoroscopic images may not good enough to see the soft tissue structures and the target structure or structures are only visible with contrast agents.

According to another exemplary embodiment the targeting method further comprises, projecting a 3D graphical model onto the fluoroscopic image. In other words, the 3D graphical model may be projected onto the fluoroscopic image. This 3D graphical model can be generated from the planned path. If the C-arm orientation is equal to the entry point orientation the 3D graphical model be projected as a circle. Preferably, the fluoroscopic image can be a so-called live fluoroscopic image, e.g. an image which is continuously or at least repeatedly recorded.

By projecting the entry point onto the fluoroscopic image an efficient way to determine an entrance point, i.e. a point at with the first object enters the second object may be provided, in particular in case the first object is moved to the entry point the entrance point may be settable by using the corresponding fluoroscopic image. Preferably, an entrance point may be determined by moving the first object to the entry point by using the fluoroscopic image.

According to another exemplary embodiment of the targeting method the predetermined shape is substantially a circle.

According to another exemplary embodiment of the targeting method the fluoroscopic image is recorded by a C-arm device.

The use of a C-arm device, i.e. an imaging apparatus having a gantry in form of a C, it may be possible to provide recorded images representing the object in different directions while the object under examination is still accessible.

According to another exemplary embodiment the targeting method further comprises recording a first plurality of fluoroscopic images of the object under examination, wherein the first plurality of fluoroscopic image is recorded under the second direction, and wherein the determining whether the first object is on the determined planned path based on a shape of the projection of the first object in the first plurality of fluoroscopic images.

The recording of several fluoroscopic images, e.g. so-called live fluoroscopic images, may be an efficient way to track the progress of the first object on the planned path, in particular whether the first object is still following the planned path. The plurality of fluoroscopic images preferably belongs to different points in time.

According to another exemplary embodiment the targeting method further comprises recording a shuttered computer tomography and determining whether the planned path has to be altered depending on the data recorded in the shuttered computer tomography. In other words, a shuttered rotational scan from which a 3D reconstruction may be made is recorded. Preferably, the shutter and/or table position, i.e. the positions at which in following CT acquisitions a shutter of the CT will be actuated, i.e. new image data will be recorded, may be calculated from the planned path as well. For example, the border positions of the slab or slice containing the planned path can be converted to shutter positions, because the relation between the volume data and the detector can be determined, and the relation between the shutters and the detector is known from the design of the geometry.

According to another exemplary embodiment the targeting method further comprises recording a second fluoroscopic image of the object under examination, wherein the second fluoroscopic image is recorded under a third direction so that a normal of the second fluoroscopic image is perpendicular to the second direction, and determining an advancing of the first object based on the second fluoroscopic image.

In other words one or several second fluoroscopic image is/are taken under an angle of 90 degrees compared to the first fluoroscopic image. On such an image the advancing of the first object in the second object can be seen in an efficient way which may lead to an improved quality of the targeting method.

According to another exemplary embodiment the targeting method further comprises generating a graphic out of the first fluoroscopic image and/or the second fluoroscopic image, and overlaying the graphic on the two-dimensional image of the object under examination. Preferably, the graphic comprises a scale. Further, from the planned path a 3D graphical model may be generated, which is visible inside the volume data. The fluoroscopic image may then overlaid with the projected volume data from the slice or slab containing the planned path and with the projected 3D graphical model of the planned path.

In this context a graphic may mean a simplified fluoroscopic image. Such a graphic can be easily overlaid on the two-dimensional image while still showing a sufficient contrast to be seen in this overlaying mode. Thus, it might be possible to display the target point on the overlaid image even in case in the fluoroscopic image the first object or the target point is only depicted showing low contrast. The implementing of a scale in the graphic may be an efficient way to measure and/or to control the advancing of the first object in the second image. Alternatively, the target point may be added into the two-dimensional, i.e. the two-dimensional image may be altered by introducing the target point as a structure. This might be advantageous in case the target point is represented by a structure having low contrast in the fluoroscopic image.

According to another exemplary embodiment the targeting method further comprises rendering the graphic and the fluoroscopic image under the same perspective. In particular, all rendering may be done with the same perspective as present in the fluoroscopic image. Preferably, a focus point in the recording of the fluoroscopic image lays on an extension of the planned path.

The rendering of the slices, volumes and/or graphics may be done with the same perspective as the corresponding fluoroscopic images in order to achieve an improved tracking of the first object in the second object. This may an efficient way to improve the targeting method by overcome a problem which might occur due to the fact that a first object, e.g. a needle, will be projected as a circle if the needle is pointed towards a focus position of the device used for taking the fluoroscopic images instead of the towards the endpoint (target point) of the planned path due to the perspective nature of the fluoroscopic images. This problem may be prevented by adapting the rotation of the C-arm in such a way that the focus position lays on the extension of the planned path line. That is, due to the perspective nature of the fluoroscopic images the object will not be projected as a circle if the detector plane is equal to the orthogonal plane of the planned path, to correct for this the orientation of the C-arm may be adapted in such a way that the focus point (e.g. X-ray source) is placed on the extension of the planned path, wherein the calculations are done from the volume coordinates to C-arm sensor coordinates.

According to another exemplary embodiment of the targeting method the first object comprises at least one marker.

The using of at least one marker on the first object may be an efficient way to improve the visibility of the first object on the fluoroscopic image.

According to another exemplary embodiment the targeting method further comprises projecting a laser onto the entry point, wherein a direction of the laser coincide with the first direction.

The provision of a laser light as a further aid for guiding or targeting a first object in a second object may be an efficient way to reduce a radiation dose of an object under examination, e.g. a patient and/or a doctor. The laser light can be placed in such a way that the laser light is placed perpendicular to the detector and shines on the entry point. With this set-up the angle of the needle is correct as long as the laser shines onto the end of the needle. Alternatively, the laser light can be used independently of the step of determining whether the first object is on the planned path based on a shape of the projection of the first object in the fluoroscopic image, i.e. the determination can be made by using the laser light instead of using the shape of the first object in the fluoroscopic image.

The examination of the object under examination, e.g. a patient, can be performed by using a C-arm device and/or by using a computed tomography apparatus, which are used to take data by a scanning unit and/or detector or detection unit. A targeting unit according to the invention, may be realized by a computer program, i.e. by software, or by using one or more special electronic optimization circuits, i.e. in hardware, or in hybrid form, i.e. by software components and hardware components. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It should be noted in this context, that the present invention is not limited to a C-arm based image and/or computed tomography, but may include the use of C-arm based 3D rotational X-ray imaging, magnetic resonance imaging, positron emission tomography or the like. In particular, the volume data used for the planning may be originating from all kinds of modalities as long as the data can be registered to the modality used for the intervention. It should also be noted that this technique may in particular be useful for medical imaging and medical targeting like targeting a needle to a predetermined target point on or in the body of a patient.

It may be seen as a gist of an exemplary embodiment of the invention that a method is provided, which comprises the use of a CT reconstruction or volume data from other modalities for determination of an entry point and a target point by selecting an appropriate slice or slab of a 3D image representation on which the entry point and the target point is indicated. A line representing the planned path connects both points. From this planned path a C-arm position is calculated in such a way that a detector plane of the C-arm is equal to the orthogonal plane of the planned path, i.e. the normal of the detector plane and the planned path are parallel. The relation between the CT volume and the detector plane is known from the so-called 3D roadmap functionality, described for example in not yet published IB2006/050733 which is hereby incorporated herein by reference. In case the 3D volume data is originating from a different modality the relation can be determined with another known registration method. The C-arm is set to the orthogonal plane of the planned path. The entry point is projected onto the live fluoroscopic images. By moving a needlepoint, i.e. the point representing a needle injected into a body of a patient, to the entry point, which are both visible on the fluoroscopic image, an entrance point into the body of the patient can be set. With a so-called bulls eyes approach the needle can now follow the planned path by changing the angle of the needle in such a way that the projected needle on the fluoroscopic image is a circle. Due to the perspective correction the detector plane is not equal anymore to the orthogonal plane of the planned path, but due to the described way of the perspective correction the needle will follow the planned path as long as the needle is visible as a circle on the fluoroscopic images. The progress of the needle can be followed by rotating the C-arm 90 degrees so that the view direction becomes perpendicular to the needle. Now a slab is selected which contains the planned path and with an orientation parallel to the detector. So-called 3D-roadmapping can now be used to blend, i.e. superimpose, the fluoroscopic image with this slab. This slab can be the same as the slab used for the planning, i.e. the determining of the planned path, if the corresponding position can be reached with the C-arm. During the procedure a number of shuttered 3D rotational reconstruction, depending on the number of images acquired CT like quality can be reached. CT acquisitions can be made to check if the planned path of the needle must be corrected for motion and/or deformation of the body of the patient and if the needle is on the expected place in the body. Thus, this exemplary embodiment proposes a method that makes it possible to perform clinical procedures, like biopsies, chemical and thermal ablation, on a rotational X-ray device, using three-dimensional roadmap functionality in combination with CT techniques. Further improvements to this exemplary embodiment may be performed by using laser light, which can be placed in such a way that the laser light is placed perpendicular to the detector and shines on the entry point. With this set-up the angle of the needle is correct as long as the laser shines onto the end of the needle, which may lead to a reduced dose for the doctor and/or patient. The needle can also be equipped with markers so that the angle of the needle can be calculated or derived from the projected marker positions on the fluoroscopic images.

A method according to an exemplary embodiment of the invention may have the advantages that an entrance point (puncturing spot) into a body as well as an entrance angle into the body may be determinable during a medical procedure. Further, the needle position in the body may be determinable during the procedure and shutter positions may be set to reduce the patient dose during a CT acquisitions to monitor the progress of the procedure.

These and other aspects of the present invention will become apparent from and elucidated with reference to the embodiment described hereinafter.

BRIEF DESCRIPTION OF THE DRAWINGS

An exemplary embodiment of the present invention will be described in the following, with reference to the following drawings.

DETAILED DESCRIPTION OF AN EXEMPLARY EMBODIMENT

The illustration in the drawings is schematically. In different drawings, similar or identical elements are provided with the similar or identical reference signs.

Figure 1:
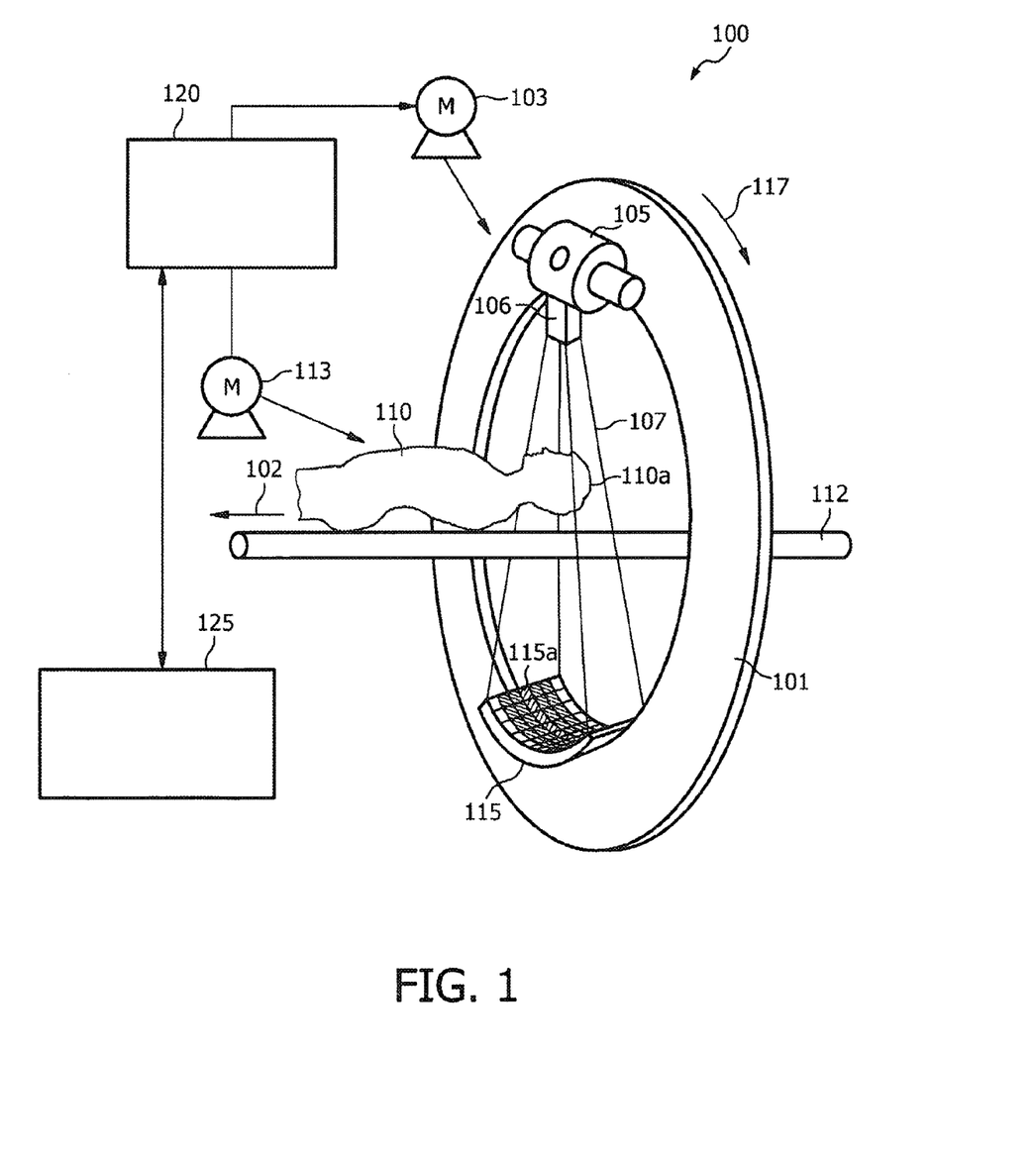
FIG. 1 shows a simplified schematic representation of a computed tomography system.

FIG. 1 shows an exemplary embodiment of a computed tomography scanner system which can be used in order to provide a three-dimensional image from which a slice can be selected. For the further targeting method a so-called C-arm device can be used which looks similar to the CT but comprises only a C-arm gantry, i.e. a gantry in form of a C, instead of a gantry, which is depicted in FIG. 1.

The computed tomography apparatus 100 depicted in FIG. 1 is a cone-beam CT scanner. The CT scanner depicted in FIG. 1 comprises a gantry 101, which is rotatable around a rotational axis 102. The gantry 101 is driven by means of a motor 103. Reference numeral 105 designates a source of radiation such as an X-ray source, which emits polychromatic or monochromatic radiation.

Reference numeral 106 designates an aperture system which forms the radiation beam emitted from the radiation source unit to a cone-shaped radiation beam 107. The cone-beam 107 is directed such that it penetrates an object of interest 110 arranged in the center of the gantry 101, i.e. in an examination region of the CT scanner, and impinges onto the detector 115 (detection unit). As may be taken from FIG. 1, the detector 115 is arranged on the gantry 101 opposite to the radiation source unit 105, such that the surface of the detector 115 is covered by the cone beam 107. The detector 115 depicted in FIG. 1 comprises a plurality of detection elements 115a each capable of detecting X-rays which have been scattered by, attenuated by or passed through the object of interest 110. The detector 115 schematically shown in FIG. 1 is a two-dimensional detector, i.e. the individual detector elements are arranged in a plane, such detectors are used in so called cone-beam tomography.

During scanning the object of interest 110, the radiation source unit 105, the aperture system 106 and the detector 115 are rotated along the gantry 101 in the direction indicated by an arrow 117. For rotation of the gantry 101 with the radiation source unit 105, the aperture system 106 and the detector 115, the motor 103 is connected to a motor control unit 120, which is connected to a control unit 125. The control unit might also be denoted and used as a calculation, reconstruction or determination unit and can be realized by a computer.

In FIG. 1, the object of interest 110 is a human being which is disposed on an operation table 112. During the scan of a head 110a, a heart, a lung or any other part of the human being 110, while the gantry 101 rotates around the human being 110, the operation table 112 may displace the human being 110 along a direction parallel to the rotational axis 102 of the gantry 101. This may be done using a motor 113. By this, the heart is scanned along a helical scan path. The operation table 112 may also be stopped during the scans to thereby measure signal slices.

The detector 115 is connected to the control unit 125. The control unit 125 receives the detection result, i.e. the read-outs from the detection elements 115a of the detector 115 and determines a scanning result on the basis of these read-outs. Furthermore, the control unit 125 communicates with the motor control unit 120 in order to coordinate the movement of the gantry 101 with motors 103 and 113 with the operation table 112.

The control unit 125 may be adapted for reconstructing an image from read-outs of the detector 115. A reconstructed image generated by the control unit 125 may be output to a display (not shown in FIG. 1) via an interface.

The control unit 125 may be realized by a data processor to process read-outs from the detector elements 115a of the detector 115.

Figure 2:
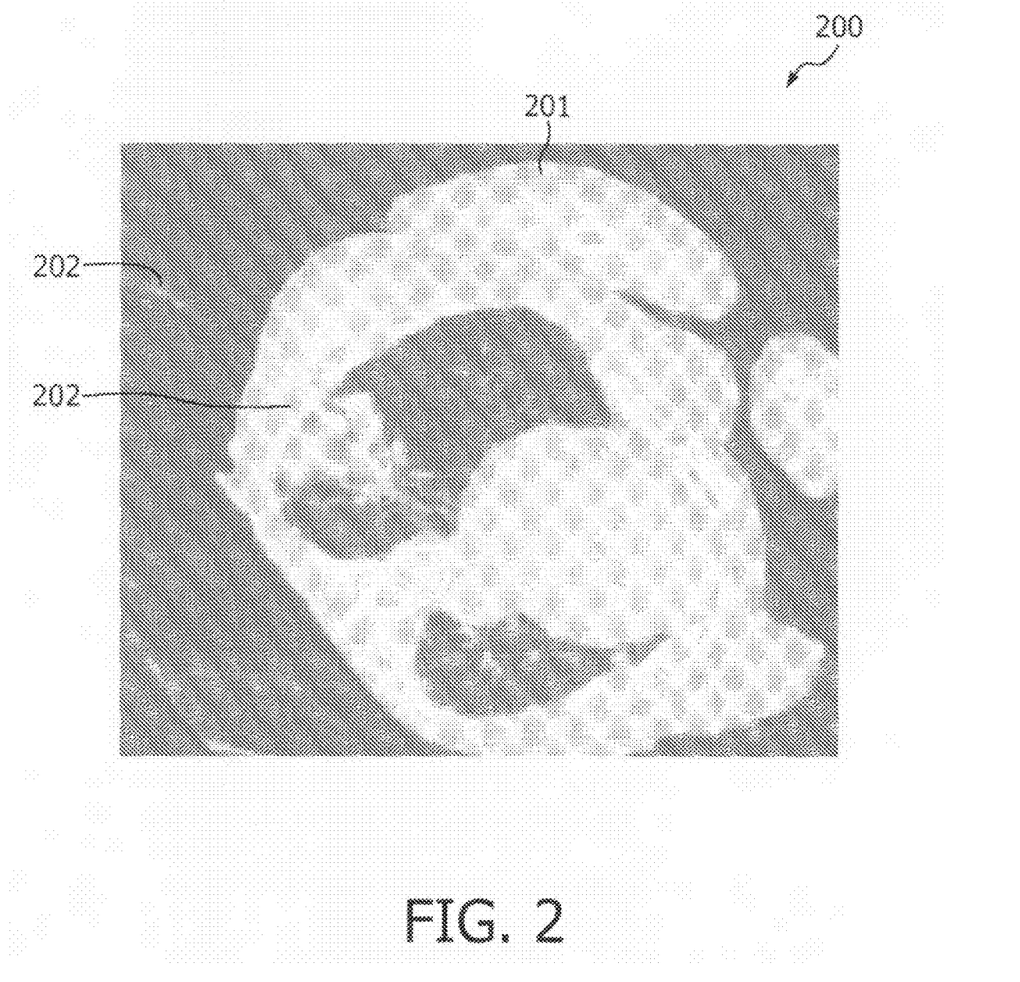
FIG. 2 shows a schematic real image of a slice of a 3D-image.

FIG. 2 shows a shows a schematic real image of a slice of a 3D-image, which can be taken and reconstructed by a CT device described with reference to FIG. 1. In FIG. 2 a cross-sectional view of a body of a patient is shown. The 3D-image 200 is taken and generated by a CT-apparatus. On the image, beside the cross-sectional view of the body 201, a needle 202 is shown which is injected into the body.

FIG. 3 shows a schematic representation of different images achieved by a method according to an exemplary embodiment of the present invention.

Figure 3A:
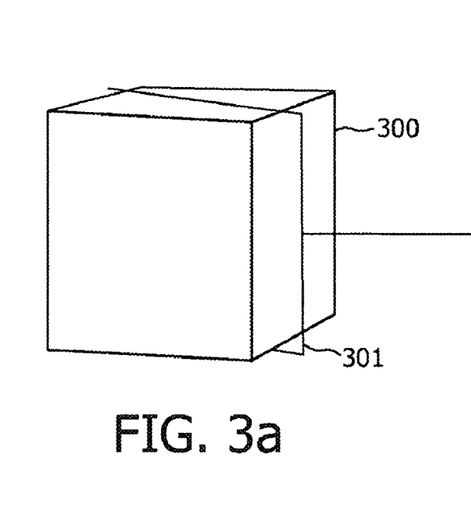
FIG. 3 shows a schematic representation of different images achieved by a method according to an exemplary embodiment of the present invention.

FIG. 3a shows, in a schematic representation, a volume 300 which can be scanned by a CT-apparatus. The line 301 depicts schematically a slice in which an entry point and a target point is present, i.e. the slice which can be used in the further procedure of the method.

Figure 3B:
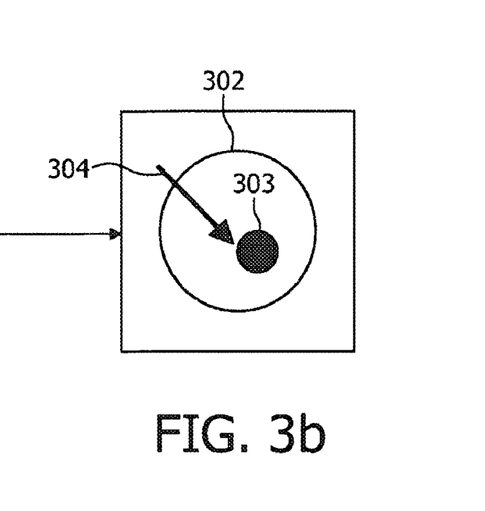

FIG. 3b schematically shows the selected slice in a simplified way. The circle 302 represents a cross-sectional view of the body under examination, while the black dot 303 represents the target point and the arrow 304 depicts schematically the planned path. The planned path is in principle a straight line connecting the entry point and the target point. From this planned path the C-arm position is calculated in such a way that the detector plane is equal to the orthogonal plane of the planned path. Furthermore, shutter positions for CT acquisitions are calculated from the planned path 304, wherein the further CT acquisitions are used to follow the progress of the injection of the needle.

Figure 3C:
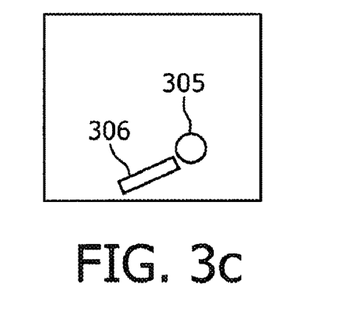

FIG. 3c schematically shows a first fluoroscopic image which is recorded under a C-arm position which corresponds to a detector plane being equal to the orthogonal plane of the planned path. In FIG. 3c a projected entry point 305 and the projected needle 306 is shown. FIG. 3c shows a stage in which the needle is not yet injected into the body. The depicted fluoroscopic image is rather used in order to define or determine the entrance point. The right position for the entrance point is achieved when the projected needle 306 contacts the projected entry point 305.

Figure 3D:
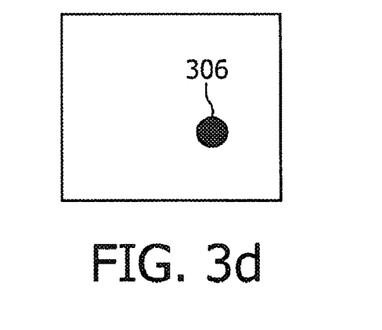

FIG. 3d schematically shows another fluoroscopic image which is recorded under the same C-arm position as FIG. 3c but after the needle is as well in contact with the entrance point and is aligned with the planned path. Thus, the projected entry point 305 and the projected needle 306 coincide in FIG. 3d. That is, the needle 306 is visible as a circle in FIG. 3d indicating that the needle is aligned with the planned path.

Figure 3E:
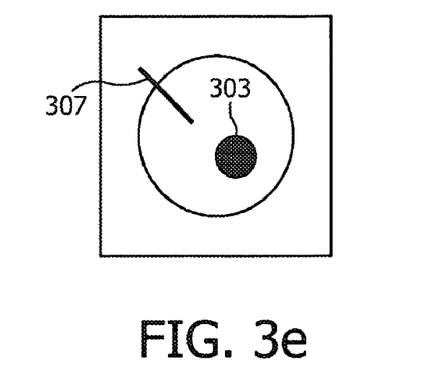

FIG. 3e schematically shows another fluoroscopic image which is recorded under a C-arm position which corresponds to a detector plane being equal to the parallel plane of the planned path, i.e. which is shifted by an angle of 90 degrees compared to the direction of FIG. 3c and FIG. 3d. Thus, the advancing of the needle 307 on the planned path to the target point 303 can be derived from FIG. 3e. For FIG. 3e a slab or slice is used which contains the planned path and with an orientation parallel to the detector. So-called 3D roadmapping can be used to blend the fluoroscopic image with this slab, i.e. to superimpose these two images. This slab can be the same as the slab used for the planning, in case the corresponding position can be reached by the C-arm.

Figure 4A:
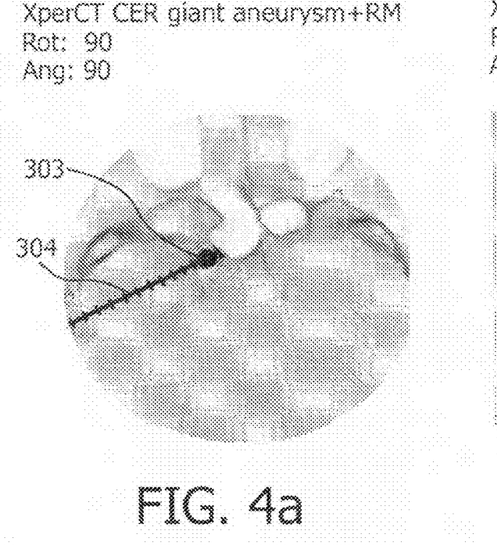
FIG. 4 shows schematic real images corresponding to images of FIG. 3.
Figure 4B:
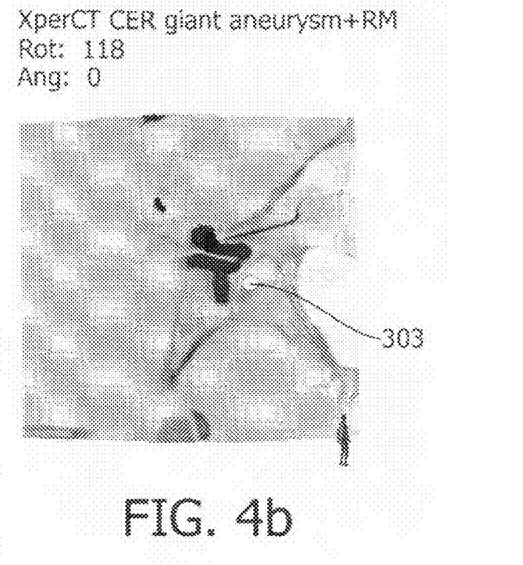
Figure 4C:
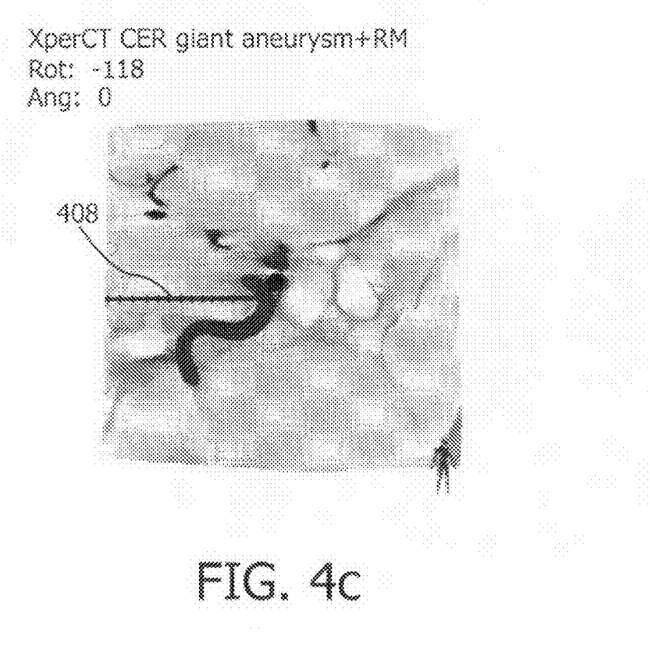

FIG. 4 shows schematic real images corresponding to images of FIG. 3. In particular FIG. 4a corresponds to FIG. 3b and shows an image of the selected slice of a body under examination showing the target point 303, the planned path 304 as well as structures of a human body. FIG. 4b corresponds to FIG. 3c, i.e. is recorded under a C-arm position which corresponds to a detector plane being equal to the orthogonal plane of the planned path. Schematically the projected entry point 305 and the projected needle 306 can be seen in FIG. 4b. FIG. 4c corresponds to FIG. 3e, i.e. is recorded under a C-arm position which corresponds to a detector plane being equal to the parallel plane of the planned path. Schematically the target point 303, the needle 306, i.e. a graphical model of the needle, and a scale 408 can be seen in FIG. 4c. The scale can be used in order to determine the advancing of the needle on the planned path.

Figure 5:
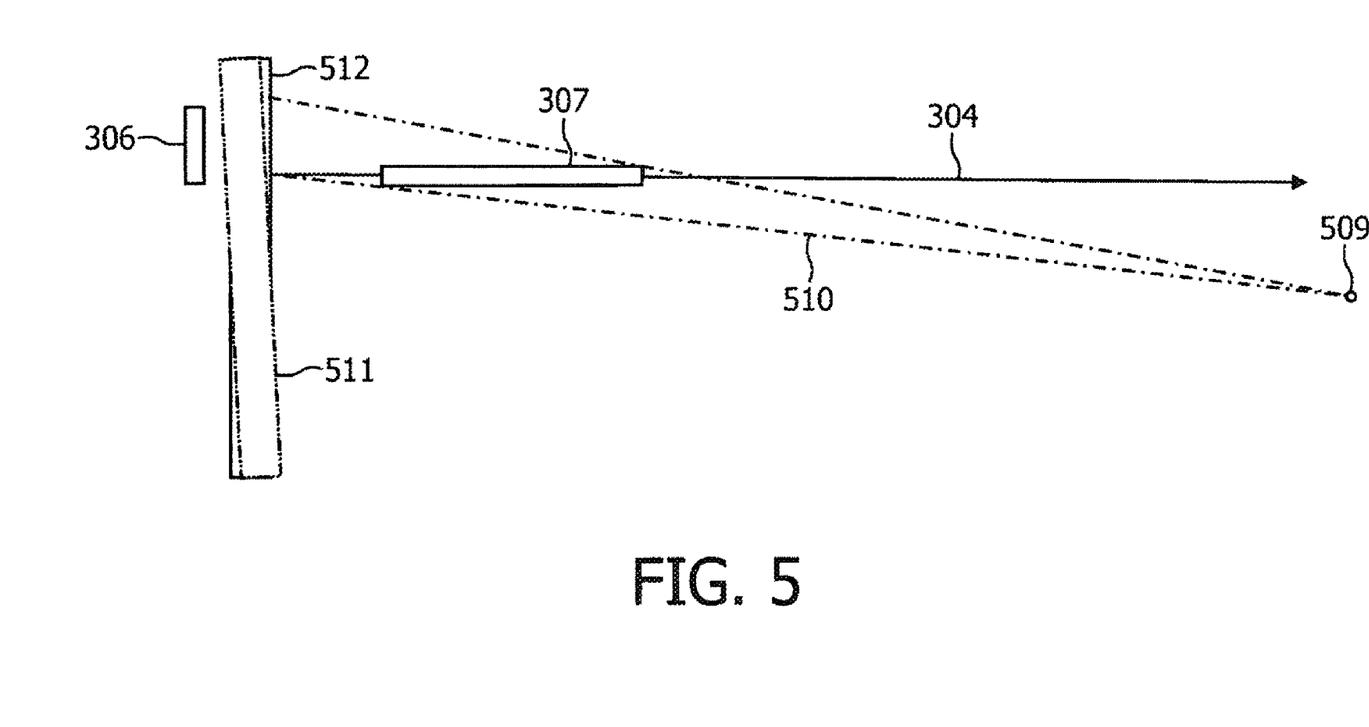
FIG. 5 shows a schematic drawing to demonstrate a perspective correction.

FIG. 5 shows a schematic drawing to demonstrate a perspective correction. As already described the so-called bull-eyes approach may provide a targeting method of slightly degraded quality due to the fact that the needle will be projected as a circle if the needle is pointed towards the focus position instead of the endpoint of the planned path due to the perspective nature of the fluoroscopic images, which can be a slightly different direction. This degradation may be prevented by adapting the rotation of the C-arm in such way that the focus position lays on the extension of the planned path. This is shown in FIG. 5. FIG. 5 shows the needle 307 which is on the planned path 304. Although, the needle 307 is correctly on the planned path 304, the projected needle 306 is depicted as a line instead of a circle. This is due to the fact that a focus position 509 of the C-arm is not on the planned path, which deviation is schematically show by the dotted lines 510. Also the detector plane 511 is shifted slightly with respect to the orthogonal direction of the planned path, i.e. is not perpendicular to the planned path. These problems can be solved by rotating the C-arm slightly in such a way that the focus position is on the extension of the planned path 304 as it is shown in FIG. 5 by the drawn through lines of the planned path 304 and the detector 512. Using this focus position the projected needle will be a circle on the fluoroscopic images in case the needle is on the planned path.

Summarizing an aspect of an exemplary embodiment of the present invention may be seen that from a planned path of a needle:

1) the C-arm position can be set in such a way that the entrance angle of the needle is equal to the viewing direction;
2) the entrance point into the body of a patient can be made visible on live fluoroscopic images;
3) the C-arm position can be set in such a way that the view direction is perpendicular to the planned path. The slabs orthogonal to the view direction are automatically selected on the base of the planned path and blended with the live fluoroscopic images.
4) shutter positions can be set in such a way that a patient dose is reduced, but still the complete progress of the needle into the body can be followed. It should be noted that the term "comprising" does not exclude other elements or steps and the "a" or "an" does not exclude a plurality. Also elements described in association with different embodiments may be combined. It should also be noted that reference signs in the claims shall not be construed as limiting the scope of the claims.

The invention claimed is:

1. A targeting method for targeting a first object from an entry point to a target point in an object under examination, the method comprising:

selecting a two-dimensional image of the object under examination depicting the entry point and the target point, the two-dimensional image acquired by a first imaging modality;

displaying the two-dimensional image on a display device;

determining a planned path from the entry point to the target point, wherein the planned path has a first direction;

recording data representing a fluoroscopic image of the object under examination utilizing a second imaging modality, wherein the fluoroscopic image is recorded under a second direction so that a normal of the second direction of the fluoroscopic image is parallel with the first direction;

displaying the fluoroscopic image on the display device;

determining whether the object is on the planned path based on a shape and/or position of a projection of the object in the fluoroscopic image.

2. The targeting method according claim 1, wherein the two-dimensional image is selected as a slice of a three-dimensional image of the object under examination.

3. The targeting method according claim 2, wherein the three-dimensional image is reconstructed out of data recorded by a computer tomography apparatus.

4. The targeting method according to claim 3, wherein the fluoroscopic image is recorded by a C-arm device.

5. The targeting method according to claim 1, further including:

projecting a 3D graphical model onto the fluoroscopic image.

6. The targeting method according to claim 1, wherein the shape is substantially a circle.

7. The targeting method according to claim 1, further including:

recording a first plurality of fluoroscopic images of the object under examination, wherein the first plurality of fluoroscopic images is recorded under the second direction;

wherein the determining whether the first object is on the determined planned path is based on a shape of a projection of a first object in the first plurality of fluoroscopic images.

8. The targeting method according to claim 1, further including:

recording data by performing a shuttered computer tomography; and determining whether the planned path has to be altered based on the data recorded in the shuttered computer tomography.

9. The targeting method according to claim 1, further including:

recording a second fluoroscopic image of the object under examination, wherein the second fluoroscopic image is recorded under a third direction so that a normal of the third direction of the second fluoroscopic image is perpendicular to the second direction;

determining an advancing of the object based on the second fluoroscopic image.

10. The targeting method according to claim 9, further including:

generating a graphic, showing the planned path and the target point, from a 3D graphical model; and overlaying the graphic on the two-dimensional image of the object under examination.

11. The targeting method according to claim 10, wherein the graphic includes a scale and further including:

rendering the graphic, the fluoroscopic images and the two-dimensional image under the same perspective.

12. The targeting method according to claim 11, wherein a focus point in the recording of the fluoroscopic image lays on an extension of the planned path.

13. The targeting method according to claim 1, wherein the object comprises at least one marker.

14. The targeting method according to claim 1, further including:

projecting a laser onto the entry point, wherein a direction of the laser coincide with the first direction.

15. The targeting method according to claim 1, further including:

determining an entrance point by moving the object to the entry point by using the fluoroscopic image.

16. A targeting device for targeting a first object from an entry point to a target point, the targeting device comprising:

a selecting unit which selects a two-dimensional image of the object under examination depicting the entry point and the target point;

a determining unit which determines a planned path from the entry point to the target point, wherein the planned path has a first direction;

a recording unit which records data representing a fluoroscopic image of the object under examination, wherein the fluoroscopic image is recorded under a second direction so that a normal of the image coincides with the first direction;

wherein the determining unit determines whether the object is on the determined planned path based on a shape of a projection of the object in the fluoroscopic image.

17. A system for targeting a first object from an entry point to a target point, the system comprising:

a radiation source;

a radiation detector; and a targeting device according claim 16, wherein the radiation detector records the data representing the fluoroscopic image.

18. The system according to claim 17, further comprising:

a computer tomography apparatus, wherein the computer tomography apparatus generates the two-dimensional image of the object under examination.

19. A non-transitory-computer readable medium in which a program for targeting a first object from an entry point to a target point is stored, which program, when executed by a processor, controls the processor to perform a method comprising:

selecting a two-dimensional image of the object under examination depicting the entry point and the target point;

determining a planned path from the entry point to the target point, wherein the planned path has a first direction;

recording data representing a fluoroscopic image of the object under examination, wherein the fluoroscopic image is recorded under a second direction so that a normal of the second direction of the image coincide with the first direction;

determining whether the object is on the determined planned path based on a shape and/or position of a projection of the object in the fluoroscopic image.

20. A method for targeting a first object from an entry point to a target point, the method comprising:

selecting a two-dimensional image of the object under examination depicting the entry point and the target point, the two-dimensional image selected as a slice of a three-dimensional image of the object under examination acquired by a first imaging modality;

determining a planned path from the entry point to the target point, wherein the planned path has a first direction;

recording data representing a fluoroscopic image of the object under examination utilizing a second imaging modality, wherein the fluoroscopic image is recorded under a second direction so that a normal of the second direction of the image coincide with the first direction;

determining whether the object is on the determined planned path based on a shape and/or position of a projection of the object in the fluoroscopic image.

21. A targeting device for targeting an object from an entry point to a larger point, the targeting device comprising:

a processor programmed to perform the method according to claim 20; and a display which displays at least one of the two-dimensional image and the fluoroscopic image.

* * * * *